US00RE36126E

United States Patent [19]

Beaty et al.

[11] E Patent Number: Re. 36,126

[45] Reissued Date of Patent: Mar. 2, 1999

[54] DENTAL RESTORATION ON ARTIFICIAL ROOT FIXTURES

[75] Inventors: Keith D. Beaty, West Palm Beach; Curtis E. Jansen, North Palm Beach, both of Fla.

[73] Assignee: Implant Innovations, Inc., Palm Beach Gardens, Fla.

[21] Appl. No.: 846,563

[22] Filed: Apr. 30, 1997

Related U.S. Patent Documents

Reissue of:

[64] Patent No.: 5,419,702
Issued: May 30, 1995
Appl. No.: 246,097
Filed: May 19, 1994

U.S. Applications:

[63] Continuation-in-part of Ser. No. 43,928, Apr. 8, 1993, Pat. No. 5,338,196.

[51] Int. Cl.[6] ..... A61C 9/00

[52] U.S. Cl. ..... 433/214

[58] Field of Search ..... 433/172, 173, 433/175, 174, 214

[56] References Cited

U.S. PATENT DOCUMENTS

| | | | |
|---|---|---|---|
| 4,086,701 | 5/1978 | Kawahara et al. . | |
| 4,758,161 | 7/1988 | Niznick . | |
| 4,842,518 | 6/1989 | Linkow et al. | 433/174 |
| 4,850,870 | 7/1989 | Lazzara et al. . | |
| 4,850,873 | 7/1989 | Lazzara et al. . | |
| 4,856,994 | 8/1989 | Lazzara et al. . | |
| 4,955,811 | 9/1990 | Lazzara et al. | 433/173 |
| 4,988,298 | 1/1991 | Lazzara et al. | 433/173 |
| 5,000,685 | 3/1991 | Brajnovic | 433/173 |
| 5,006,069 | 4/1991 | Lazzara et al. . | |
| 5,015,186 | 5/1991 | Detsch | 433/173 |
| 5,030,096 | 7/1991 | Hurson et al. . | |
| 5,035,619 | 7/1991 | Daftary | 433/173 |
| 5,040,983 | 8/1991 | Binon . | |
| 5,071,351 | 12/1991 | Green, Jr. et al. . | |
| 5,073,111 | 12/1991 | Daftary | 433/173 |
| 5,100,323 | 3/1992 | Friedman et al. . | |
| 5,135,395 | 8/1992 | Marlin | 433/174 |
| 5,145,371 | 9/1992 | Jorneus . | |
| 5,145,372 | 9/1992 | Daftary et al. . | |
| 5,188,800 | 2/1993 | Green, Jr. et al. . | |
| 5,209,659 | 5/1993 | Friedman et al. . | |
| 5,209,666 | 5/1993 | Balfour et al. . | |
| 5,213,502 | 5/1993 | Daftary . | |
| 5,281,140 | 1/1994 | Niznick . | |
| 5,292,252 | 3/1994 | Nickerson et al. . | |
| 5,297,963 | 3/1994 | Daftary | 433/172 |
| 5,334,024 | 8/1994 | Niznick | 433/173 |
| 5,338,196 | 8/1994 | Beaty et al. | 433/172 |
| 5,431,567 | 7/1995 | Daftary . | |
| 5,433,606 | 7/1995 | Niznick et al. | 433/173 |
| 5,547,377 | 8/1996 | Daftary . | |
| 5,564,921 | 10/1996 | Marlin | 429/224 |

FOREIGN PATENT DOCUMENTS

| | | |
|---|---|---|
| 0 442 855 A1 | 8/1991 | European Pat. Off. . |
| 1291470 | 10/1972 | United Kingdom . |

OTHER PUBLICATIONS

Exhibit A, a drawing of a healing abutment.

Exhibit A, an assembly drawing of a coping and the component drawings which comprise the coping assembly.

Lewis, S.G. et al., *Single Tooth Implant Supported Restorations*, Intnatl. Jrnl. of Oral & Maxillofacial Implatns, vol. 3, No. 1, pp. 25–30, 1988.

(List continued on next page.)

*Primary Examiner*—Cary E. O'Connor
*Attorney, Agent, or Firm*—Arnold, White & Durkee

[57] ABSTRACT

A second stage healing abutment for forming and preserving in the mucosa above a dental implant a transmucosal opening large enough to receive an artificial tooth that faithfully replicates a natural tooth being restored, and a companion transfer coping having identical transmucosal portions for forming in a laboratory model a faithful replica of the transmucosal opening made of a resilient gingiva replicating material in which to fabricate the artificial tooth, and methods of using the same.

8 Claims, 2 Drawing Sheets

OTHER PUBLICATIONS

Lewis, S.G. et al., *The "UCLA" Abutment,* Intnatl. Jrnl. of Oral & Maxillofacial Implants, vol. 3, No. 3, pp. 183–189, 1988.

Perri DDS, George et al., *Single Tooth Implants,* CDA Journal, vol. 17, No. 3, Mar. 1989.

DIA™ Dental Imaging Associates, Implanted—The Source, "The Anatomical Abutment System", Copyright Date Oct. 9, 1991 on p. 10. (Front Cover, pp. 1–10 and Back Cover).

Steri–Oss®, Product Catalog, Feb. 1992, Cover Page, pp. 7–14, and Last Page.

Branemark System (Nobelpharma), Product Catalog Prosthetics, 1991, 24 pages.

Steri–Oss®, Product Catalog, Sep. 1990, 36 pages.

IMTEC Hexed–Head™ Implant System, Spring 1993 Catalog, 15 pages.

Interpore International, IMZ™ Prosthetic Flow Chart, Jul. 1993, 2 sheets.

Impla–Med, Catalog, Mar. 1991, 16 pages.

Stryker Dental Implants, Catalog Data Sheets, Undated, 4 sheets.

Stryker Dental Implants, Price List, Jun. 1, 1993, 46 pages.

Oratronics, Inc., "Options for Oral Implantology . . . Oratronics Endosseous Tri–Dimensional T–3D Oral Implant Healing System (OIHS)", 1978 8 pages.

DENTAL RESTORATION ON ARTIFICIAL ROOT FIXTURES

Matter enclosed in heavy brackets [ ] appears in the original patent but forms no part of this reissue specification; matter printed in italics indicates the additions made by reissue.

This application is a continuation-*in-part* of application Ser. No. 08/043,928, filed Apr. 8, 1993, now U.S. Pat. No. 5,338,196.

BACKGROUND OF THE INVENTION

The field of restorative dentistry using artificial roots in the presently preferred form of osseointegrated cylinder shaped dental implants has progressed to the level where attention is now being given to providing restorations on them that closely replicate natural dentition in appearance, especially where the teeth emerge from the gums. The problems of achieving a natural looking emergence profile are addressed using a technique for fabricating implant supported restorations directly to an implant, employing custom wax patterns fashioned on abutment cylinders to achieve, for example, a custom made porcelain fused to metal restoration. This technique is described in published articles that appeared in The International Journal of Oral & Maxillofacial Implants, Vol. 3, Number 1, 1988 at pages 25–26 "Single Tooth Implant Supported Restorations" Lewis, S. G. et al., and Number 3, 1988 at pages 183–189 "The 'UCLA' Abutment", Lewis, S. G. et al. A similar result using a different abutment is described in U.S. Pat. No. 4,928,298, which is owned by the Assignee of the present invention. The problem is incompletely addressed in U.S. Pat. No. 5,073,111 issued to Daftary Dec. 17, 1991.

The dental restoration of a wholly or partially edentulous patient with dentition supported on dental implants is now frequently done in two stages. In the first stage the implant is placed and left to integrate with the jawbone. The second stage begins with re-accessing the implant through the gum and maintaining access with a healing cap or the like, and continues through the fabrication of restorative dentition in the laboratory using measurements and other information taken from time to time from the patient. During that time the patient may have only a healing cap in his or her mouth, or according to more recent and sophisticated procedures the patient may be fitted with temporary dentition from which additional refining measurements can be taken. Nevertheless, the healing abutments and the transfer copings, or pick up copings, of the prior art do not cooperate to provide room for making and installing on the implant an artificial tooth having an aesthetically pleasing or anatomically correct emergence profile. The gingival aspect of an implant is, typically not more than about 4.1 mm in diameter, whereas the longer (mesial-distal) dimension of a natural tooth where it emerges from the gum is between about 4.5 mm and about 8.0 mm. According to present practice, healing abutments, which are cylindrical in cross section, are chosen to approximate the mesialdistal dimension of the tooth being replaced. At the same time, the transfer, or pick up, copings of the prior art are all one size, about 4.5 mm in diameter. As a result, a gap is left in the gingiva, around the coping, and impression material fills this gap when an impression is taken. The gingiva also tends to collapse into this gap, resulting in less than accurate replication of the conditions in the patient's mouth. As a further consequence of these problems, it is difficult to make soft tissue models accurately. Stone models replicate these errors, and this requires technicians to shape the stone manually to comply with the conditions in the patient's mouth, or risk producing a crown with an inaccurate emergence profile or crown to abutment margin that is misplaced. These are severe problems, resulting from the fact that the designers of prior art components have thus far failed to recognize them. The present invention teaches new surgical and laboratory components, and new procedures, which eliminate such inaccurate and time wasting procedures, and improve the art of making anatomically correct and aesthetically pleasing dental restoration.

GENERAL NATURE OF THE INVENTION

In accordance with the present invention, a healing cap or healing abutment sized to maintain space for a desired emergence profile through the gum is used at the beginning of the second stage, in combination with an impression coping, or a pick up coping, having similar size specifications so that when the impression coping is fitted to the implant for taking the impression from which the model will be made the space for the desired emergence profile established in the gum by the healing abutment, or cap, will be preserved and replicated in a stone model and in a soft tissue model, if desired. From such models restorative dentition can be fabricated without requiring the use of a specially contoured tooth support abutment as taught Daftary, for example. Rather, artificial teeth replicating in all material respects the natural teeth that they replace can be fashioned on the model using components that have become standard in the art.

In one of its aspects the invention teaches a new method of preparing an aesthetically pleasing, as well as anatomically correct dental restoration on a natural or artificial root comprising first the step of preparing in the gingiva overlying the root an opening to the gingival aspect of the root, which opening is sufficient to accommodate the shape and contour of a natural tooth emerging through the gingiva from the root, followed by the step of making a model that reproduces in stone or in overlying soft tissue exactly that opening and gingival aspect of the root, and then the step of forming on the model an artificial tooth that replicates in that opening the shape, dimensions and contour desired in the restoration, and finally installing that restoration on the root. In another aspect, the invention provides a healing member (sometimes called a cap) that has a transmucosal section having at one end the subgingival cross sectional dimensions and contours of the artificial root and where it emerges from the gingiva the mesial-distal size of the natural tooth being replaced, and means to attach that healing member non-rotatively to the root, for establishing the above mentioned opening in the gingiva. In another aspect, the invention provides a transfer coping for use in making the above mentioned model having a transmucosal section that is substantially identical in cross sectional dimensions and contours to the transmucosal section of the healing member so as to fit fully within the opening in the gingiva that was formed by the healing member, and a supragingival section shaped for non-rotational embedment in resilient modelling material, together with means to attach the coping non-rotatively to the root. In still another aspect, the invention provides sets of matched pairs of healing members and transfer copings shaped and sized for use according to the invention to prepare restorations of particular types of teeth, such as molars, premolars, bicuspids, and incisors, as examples.

These and other features of the invention will be explained in greater detail in the following description of certain exemplary embodiments of the invention referring to the accompanying drawings in which.

DETAILED DESCRIPTION OF THE DRAWINGS

Figure 1:
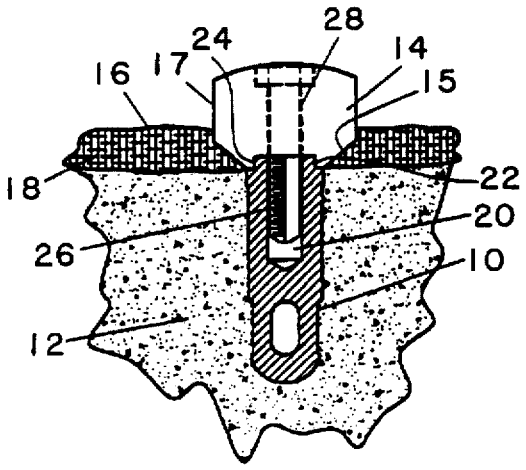
FIG. 1 is a longitudinal section that shows an implant installed in a bone with a healing cap in place.

FIG. 1 schematically illustrates a dental implant 10, or root means, of the osseointegrated type installed in a section of jawbone 12. The "second stage surgery" has begun, and a healing abutment 14 is in place on the implant. In order to provide for a more natural emergence profile in the final restoration, this abutment expands in a tapered transmucosal section 15 from the end contacting the implant toward the outer surface 16 of the surrounding gingiva 18, beyond which the walls 17 of the abutment may extend vertically. As shown in FIG. 1, a portion of the vertical walls 17 is immersed in the gum tissue, below the outer surface 16, together with the tapered section 15. The implant has an internally threaded bore 20 axially located in it, surrounded at its gingival opening by a non-round boss 22, the external cross section of which typically is hexagonal. The healing abutment 14 has a corresponding non-round socket 24 enveloping the boss 22. In the illustrated embodiment through-bolt 26 passing through an axial bore 28 in the healing abutment is used to attach the abutment to the implant, in a well known matter. Attached in this manner, the healing abutment is not able to be rotated around the axis of the bolt. Healing abutments according to the invention may be prefabricated with a transmucosal section 15 having at the gingival surface 16 a round cross sectional shape the diameter of which is approximately equal to the mesial-distal dimension of the lost tooth being restored. Alternatively, the peripheral contour in the tapered section 15 may closely replicate the emergence profile of the natural tooth that was in the site where the implant 10 is installed. The invention contemplates providing sets of such prefabricated healing abutments, together with matching impression copings. The supragingival vertical walls of the healing abutment and the impression copings used with it may also be contoured to mimic the natural tooth cross-section, or may have a diameter replicating the width of the natural tooth where it emerged from the gingiva, depending on the thickness of the gingiva 18 and the corresponding vertical dimension of the abutment.

Figure 2:
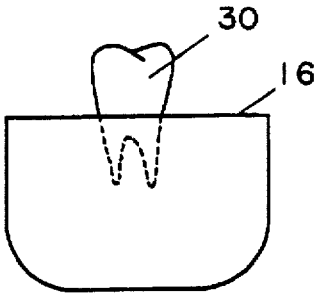
FIG. 2 shows a natural bicuspid.

FIG. 2 shows the general contours of a bicuspid 30 emerging from the outer surface 16 of the gingiva. A typical bicuspid is approximately 5.5 mm in mesial-distal dimension at the surface 16. A typical standard abutment or impression coping is at most 4.5 mm in diameter. Some teeth, e.g., molars, may be as much as 6.0 or 7.0 mm in mesial-distal dimension. Moreover, as appears in FIG. 6, which illustrates the cross section of an emergence profile 75 characteristic of an anterior tooth (not shown), it is also desirable to be able to provide for emergence profiles the cross sections of which do not even approximate round. To address these problems the invention provides methods and means to create and preserve openings in the gingiva 18 that are significantly larger than the cross section of the implant 10 and that may be round, or may have any desirable shape, and to preserve each such opening throughout the laboratory procedure for making and fitting the relevant dental restoration. Thus, as has been mentioned, the cross sectional shape of the transmucosal tapered portion 15 and the vertical wall portion 17 of the healing abutment can be round as long as its diameter approximates the mesial-distal size of the natural tooth.

Figure 3:
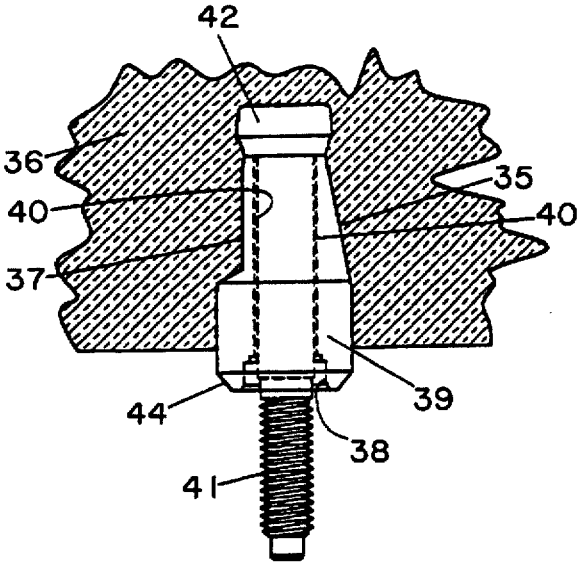
FIG. 3 is a longitudinal section that shows a transfer coping used to make an impression.

FIG. 3 shows a transfer coping 35 of a kind used to take impressions, buried in an impression material 36. The essential structure of this impression coping is described and claimed in U.S. Pat. No. 4,955,811, which is owned by the Assignee of the present invention. This impression coping has a flat surface 37 for locating it non-rotationally in the impression material, a hexagonal socket 38 in its base 39 for fixing it non-rotationally on the implant 10, an axial through bore 40 and a bolt 41 with an expanded head 42 for holding it in the impression material. The bolt 41 is used to attach the impression coping 35 to the implant 10. For the purposes of the present invention, the impression coping has a tapered section 44 at its end surrounding the socket 38 that replicates in size and shape the tapered transmucosal section 15 of the healing abutment 14. As shown in FIG. 3, a portion of the base 39 emerges from the impression material 36, together with the tapered section 44. The base 39 may also be contoured to mimic the natural cross section of the tooth being replaced, as is mentioned above, or may have a diameter replicating the width of the natural tooth where it emerged from the gingiva.

Figure 4:
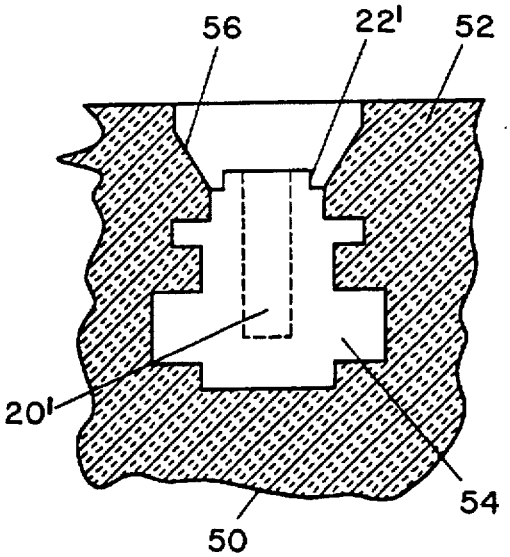
FIG. 4 is a longitudinal section that shows a stone model made from the impression.

FIG. 4 is a stone model 50 of the patient's implant installation site shown in FIG. 1. An implant replica 54 is encased in stone 52, according to well known dental laboratory practice. The replica 54 has a threaded bore 20' and a non-round boss 22' that are identical to the bore 20 and boss 22 of the implant 10. A tapered recess 56 in the surface of the stone surrounding the end of the replica 54 matches in size and shape the tapered section 44 and a part of the base 39 of the impression coping 35. Thus, the healing abutment fits equally well on the implant replica as on the implant.

The illustration in FIGS. 1,3, and 4 of a process in which the openings in the gingiva 18 and the model 50 have a "vertical" portion as well as the tapered portion is exemplary only, and is not intended to limit the invention to that feature.

Figure 5:
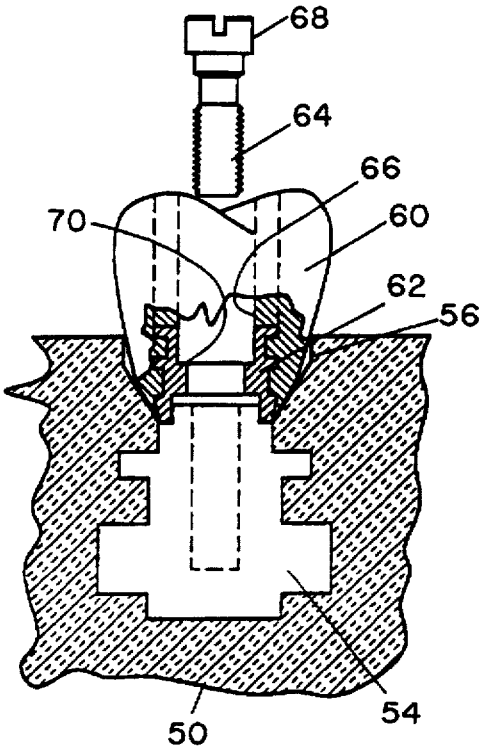
FIG. 5 shows the invention as used to replicate the natural tooth of FIG. 2.

An artificial bicuspid 60, as shown in FIG. 5, can be made with the aid of the model 50. A known form of core 62 is non-rotatively attachable to the implant replica with a screw bolt 64, passed through a through bore 66 in the core. The head 68 of the bolt comes to rest on a shoulder 70 in the core 62, holding the core firmly attached to the implant replica 54 within the tapered recess 56. The artificial tooth is fashioned on the core using any available dental material, such as porcelain or acrylic, for example. The dental material extends well within the tapered recess 56, so that outside this recess the core material cannot be seen. The core itself can be made of any suitable rigid material, such as titanium and its dilute alloys. After being fashioned and anatomically shaped as desired, the artificial tooth 60 can be transferred to the implant 10 and its appearance will be as is shown in FIG. 2. It will emerge from the gingiva 18 looking exactly the same as a natural tooth. According to well known dental practice, the opening into the core at the top of the tooth 60 will be filled with a suitable dental cement or the like, and polished so as to be for all practical purposes not distinguishable from the rest of the tooth. The above mentioned U.S. Pat. No. 4,988,298 illustrates an artificial tooth that can benefit from the invention.

Figure 6:
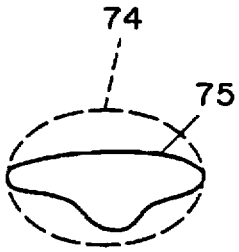
FIG. 6 shows the cross section of a natural emergence profile that the invention can replicate.

Because the component parts used in this invention can be made so that they are non-rotatably attachable together, it is not necessary that they be cylindrical in cross section where they are attachable one to the other. Thus, the healing abutment 14, the base 39 of the impression coping 35, and the subgingival section of the artificial tooth 60 can each be given the same cross sectional dimensions and contours, changing gradually from round at the sub gingival aspect of the implant 10 to non-round proceeding toward the gingival surface through which the artificial tooth will emerge from the surface 16 of the overlying gingiva. In this manner that size and shape can initially be established by the healing abutment in the opening through the gingiva 18, and the same size and shape in the correct orientation around the axis of the implant 10 can be replicated and preserved in the model 50, thereby enabling the tooth 60 to be formed in the laboratory with the correct emergence profile. This feature of the invention is particularly advantageous when restoring anterior dentition, where the emergence cross section, e.g., 75 as is indicated in FIG. 6, has segments that are almost straight, and curved segments that turn on short radii.

The invention is not limited to the use of non-rotatively attachable components. In its more general aspects, the invention contemplates providing transmucosal openings that may be round with a diameter that approximates the mesial-distal dimension of the missing tooth that is being replaced, and preserving that dimension in a round opening throughout the laboratory procedure. This simple arrangement provides the basic advantages of the invention, which include eliminating the need to surgically expand a trans-tissue opening that was originally, or has become, too small to receive the restoration, and eliminating the need for laboratory technicians to hand finish stone models in which the trans-tissue opening was incorrectly formed due to causes that are mentioned above. Provided the trans-tissue opening is formed and maintained large enough to receive the restoration, last minute surgery is not needed, and the tissue will grow to the restoration. Referring to FIG. 6, the dashed line circle 74 represents a trans-tissue opening that is larger then the tooth 75. In this situation, there is no need to provide the non-rotative features such as the mating non-round boss 22 and socket 24.

According to the invention, healing abutments 14 and transfer copings 35 may be prefabricated in sets of pairs, each pair having an "emergence profile contour" that is representative of a range of teeth of a particular type; that is, for example, large molars, small molars, premolars, bicuspids, and anterior incisors. The restorative dentist may then choose a pair that most closely replicates the emergence profile that is desired, modify the members of that pair if such is deemed necessary or desirable, and them make a restoration in accordance with the present invention that will be aesthetically pleasing and very close to anatomically correct.

Figure 7:
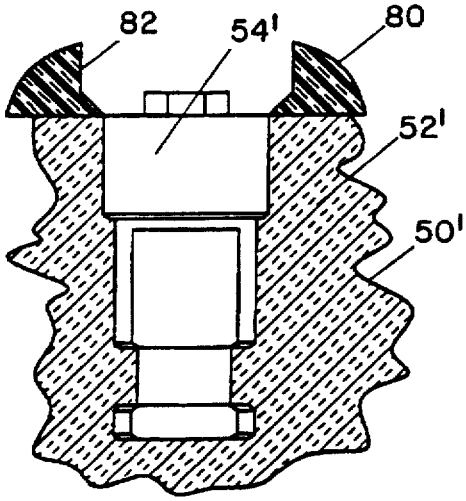
FIG. 7 is a cross section that shows a soft issue model.

FIG. 7 shows a stone model 50' similar to the model 50 of FIG. 4, but in cross section rather than in longitudinal section, and including a stone foundation 52' rigidly holding an implant replica 54'. A soft tissue layer 80, which replicates the human gingiva 18, overlies the stone part. This layer can be made of any suitable plastics or rubber-like material having physical properties such as softness and elasticity that resemble the physical properties of human gum tissue. Certain silicone based rubber and plastics materials are suitable, preference being given to those that can be fabricated from a soft flowable state. In use, the soft flowable plastics material is placed in the impression around the tapered section 44 and emerging portion of the base 39 of the transfer coping 35 to a thickness the same as that of the patient's gingiva 18. The resulting opening 82 is similar to the opening 56 in the stone that is shown in FIG. 4. It has the advantage that the laboratory technician can manipulate the model exactly as the dentist manipulates the patient's gingiva. The best results are obtained if different silicone based products are used for the impression material and the replication of the gingiva opening. For example, polysulfides, polyethers, polyvinyl, or other similar silicone products may be used. The use of two different materials helps to prevent bonding between the gingiva replication material and the impression material.

Other advantages of the resilient gingiva replication material include the opportunity of the laboratory technician to remove the gingiva replication material from the stone model, such as to access the implant replica, if desired. In addition, stone models of the prior art may fracture when lifting the models from the impression material if the transfer copings are not normal to the model. The replication material absorbs load from the transfer copings when lifting the stone model with the transfer copings attached from the impression material.

Figure 8:
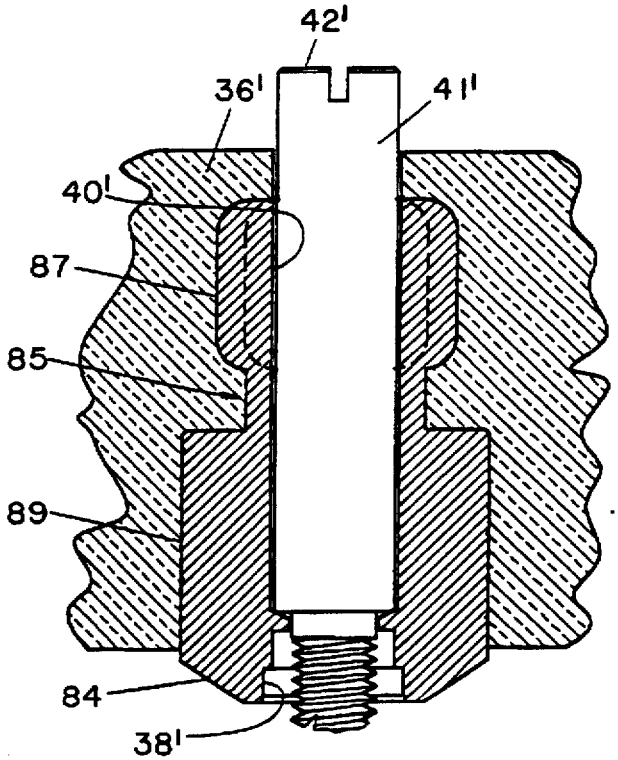
FIG. 8 shows a pick up coping used to make an impression.

FIG. 8 shows a pick-up coping 85 buried in an impression material 36'. This impression coping has a non-round head portion 87 for anchoring the coping nonrotationally on the implant, if desired, an axial through bore 40' and a bolt 41' passing through this bore to attach the impression coping to the implant. The proximal end 42' of the bolt has no expanded head on it for the reason that in use when an impression is taken, this end of the bolt extends through a hole in the impression tray (not shown) and, when the impression material has set up in the tray the bolt 41' is unscrewed from the implant by accessing its proximal end 42' from the outside the tray, and the coping 85 remains in (is "picked up" by) the impression material, being anchored therein by its expanded head 87. For the purposes of this invention, the pick up coping 85 functions like the transfer coping 35 of FIG. 3. Thus, the base 89 is expanded to a diameter that approximates the mesial-distal dimension of the natural tooth that is being restored and the tapered section 84 reduces subgingivally to the diameter of the implant or other underlying support that may be present. Like the base 39 in FIG. 3, the base 89 may be contoured to mimic the cross section of the natural tooth, or may have a diameter replicating the width of the natural tooth where it emerged from the gingiva.

We claim:

1. A dental model for fabricating a dental restoration for installation on root means in the site of a natural tooth with an overlying gingiva layer having an opening to the root means, which comprises:

a solid portion representing bone at said site;

a resilient gingiva-replicating material over the solid portion having an opening therein for replicating the gingiva opening and surrounding natural gingiva;

said opening in said gingival-replicating material having dimensions and contours of a shape approximately replicating the emergence profile of the natural tooth where the natural tooth emerged from the gingiva; and a replica of the root means in the solid portion at the bottom of said opening in said gingiva-replicating material.

2. The model of claim 1 wherein the resilient gingiva-replicating material has a thickness substantially the same as the thickness of the overlying natural gingiva at the site of the natural tooth.

3. The model of claim 1 wherein said opening in said gingiva-replicating material has a diameter substantially replicating the width of the natural tooth where the natural tooth emerged from said gingiva.

4. The model of claim 1 wherein the gingival aspect of said root means is replicated.

5. A dental model on which to fabricate a dental restoration for installation on root means in the site of a natural tooth, said model comprising a solid material representing bone at said site overlaid with soft material representing gingiva at said site, an opening through said soft material substantially replicating the major cross-sectional dimensions of said natural tooth between its host jawbone at said site and the surface of gingivae overlying said jawbone at said site, the cross-sectional dimensions of said opening expanding gradually from said solid material to the remote surface of said soft material substantially to accommodate said cross-sectional dimensions of said natural tooth, and a replica of said root means in said solid material at the bottom of said opening.

6. A model according to claim 5 in which said soft material has a thickness substantially the same as the thickness of natural gingiva overlying the jawbone at the site of said natural tooth.

7. A model according to claim 6 in which the gingival aspect of said root means is replicated.

8. A model according to claim 7 substantially replicates the gingival aspect of a dental implant fixture.

* * * * *